US00PP08116P

United States Patent [19]

Yoshida et al.

[11] Patent Number: Plant 8,116

[45] Date of Patent: Jan. 26, 1993

[54] NECTARINE TREE 'CHIYODARED'

[75] Inventors: Masao Yoshida, Morioka; Hidetoshi Kyotani, Tsukuba; Masami Yamaguchi, Sagae; Teruo Kozono, Tsukuba; Teruo Nishida, Mito; Yuri Ishizawa, Tsukuba; Kitsuo Kanato, Nagoya; Koichi Nishimura, Tsukuba, all of Japan

[73] Assignee: Fruit Tree Research Station, Ministry of Agriculture, Forestry and Fisheries, Tsukuba, Japan

[21] Appl. No.: 667,928

[22] Filed: Mar. 12, 1991

[51] Int. Cl.[5] ..... A01H 5/00

[52] U.S. Cl. ..... Plt./41.1

[58] Field of Search ..... Plt./41, 41.1

[56] References Cited

U.S. PATENT DOCUMENTS

P.P. 6,753 4/1989 Zaiger et al. ..... Plt. 41

P.P. 7,186 3/1990 Taylor ..... Plt. 41

*Primary Examiner*—James R. Feyrer

*Attorney, Agent, or Firm*—Armstrong & Kubovcik

[57] ABSTRACT

Disclosed is a nectarine (*Prunus persia*) tree of a medium vigor and spreading, foliated with large elongated leaves, and producing uniform, medium size, round to round-elliptic shaped clingstone fruit having a yellow ground color and deep red overcolor skin, and a yellow flesh which is slightly red near the pit.

5 Drawing Sheets

BACKGROUND OF THE INVENTION

1. Field of the Invention

The present invention relates to a new and distinct variety of nectarine (*Prunus persia* Batsch var. nucipersica Schneid) tree having a moderate vigor and moderate productivity, and bearing a round to round-elliptic shape fruit with a soft, melting and juicy flesh.

2. Description of the Related Art

In Japan, some varieties of nectarine have been introduced in an attempt to culture a cultivar, but these varieties were not a success. We, however, have engaged in an extensive and continuing plant breeding program at our experimental nursery and orchard located in the central part of Kantō district, Japan, for many years, and have bred a nectarine variety 'Hiratsuka Red' having a bright color skin and a characteristic tasting flesh in 1981. One purpose of this was to provide an improved nectarine tree having fruit which matures early in the season and having the same or a higher quality taste as the prior cultivars.

The characteristics of cultivars of nectarine for comparison and origin are as follows:

'Hiratusukared' is a cultivar producing a fruit with a yellow flesh and is a medium ripening cultivar (i.e., the ripening time is from July 29 to August 6 at the Nagano Fruit Tree Experimental Station, Nagano prefecture, Japan). It is similar to 'Nectared 5'. The tree was obtained by crossing, 'Okitu', which has easy fruit cracking, and 'NJN 17', and has an excellent quality flesh.

'Nectared 5' is a cultivar producing a fruit with a yellow flesh and an excellent quality. Middle ripening as with 'Hiratsukared'. The cultivar has been bred in New Jersey, U.S.A.

'Wase-Nectarine' is a cultivar producing a fruit with a yellow and melting flesh, and medium acidity. This cultivar has a fruit of the same type of eating quality as 'Hiratsukared', 'Nectared 5', and the present variety 'Chiyodared'.

These cultivars are distinguished from each other as follows:

Between 'Wase-Nectarine' and 'Hiratsukared' they have different ripening dates, level of coloring, and size of the fruit. The ripening date of the former is about one week earlier than that of the latter, but has about 30–40% smaller size fruit.

The cultivar 'Nectared 5' is a fruit with a deeply colored skin and is significantly different from 'Wase-Nectarine' having a fruit with a lightly-colored skin.

The present cultivar 'Chiyodared' has the same color fruit as 'Nectared 5', and is distinguishable from 'Wase-Nectarine' in the skin color thereof. Furthermore, the ripening time of 'Chiyodared' is earlier than that of 'Wase-Nectarine'.

ASEXUAL REPRODUCTION OF THE VARIETY

The new variety of nectarine tree is a cross-seedling which was originated from a crossing between 'Hiratsukared' (♀) and 'Nectared 5' in 1973 at the Horticultural Research Station of the Ministry of Agriculture, Forestry and Fisheries, at Hiratsuka-shi, Kanagawa-ken, Japan. A seed obtained from the cross-seedling was bred, to obtain a seedling and then the seedling, number N-45-10, was planted in a breeding field at Chiyoda-mura, Niihari-gun, Ibaraki-ken, Japan, in 1974. A tree bred from the seedling first bore fruit in 1976. For the next three years, inspection growing tests of the tree and quality test of the fruit, were carried out for the first selection, in 1978. As a result, it was found that the tree has excellent characteristics, and thus a second selection of the tree as made and the tree subjected to the fourth local adaptability test under strain number Peach-Tsukuba No. 76, in 1980. In 1989, it was confirmed that the tree is able to produce a cultivar and that the fruit has an excellent dessert quality. Thus, this new variety of nectarine tree according to this invention was judged to be an excellent new cultivar, and was given the denomination 'Chiyodared'.

We asexually reproduced this new and distinct variety of nectarine tree 'Chiyodared', by grafting, at the Fruit Tree Research Station, Ministry of Agriculture, Forestry and Fisheries, at 2-1, Fujimoto, Tsukuba-shi, Ibaraki-ken, Japan, and confirmed the homogeneity and stability of 'Chiyodared' according to this invention.

An application for this new variety of nectarine tree 'Chiyodared' under the Seeds and Seedling Law of Japan was filed on Mar. 31, 1989, under application number 3329, and is now pending.

SUMMARY OF THE INVENTION

This new variety of nectarine (*Prunus persica*) tree according to the present invention has a medium spread (i.e., 5-5.5 meters in height and 6-6.5 meters in width, as observed from an appropriately pruned specimen 8-10 years old), natural tree shape is upright, a slightly strong vigor, a medium occurrence and slightly stout shoot (i.e., branching is medium in density and branches are of average strength), the crotch angles formed by branches are about 60°, a medium internode, a green ground color which becomes reddish brown when exposed to the sun, a foliated large and yellowish-green leaf, a medium predominance of flower bud, which are mixed single and multiple buds, a medium flowering with single and pink petals, a medium pollen, an excellent fruit bearing, and flowers a few days earlier than both 'Wase-nectarine' and 'Hiratsukared'. The tree produces a round to round-elliptic and uniform shaped fruit about 170 g in weight, and having a slightly broad, shallow stylar end and a shallow suture. The skin of the fruit has a yellow ground color which becomes a deep red over all of the skin without pubescence, is glossy and has a little fruit cracking. The flesh is yellow and slightly red near the pit, soft, i.e., slightly fine to medium, melting and juicy, and has a good texture, a moderate sweetness and high sourness, i.e., the pH of the juice is about 3.5, a slight aromatic flavor, and no astringency, and thus has an excellent dessert quality. The pit is a cling-stone having a obovoid, of a medium size and light brown in color. The fruit has a good keeping quality compared with 'Wase-nectarine', and about a week earlier than 'Wase-nectarine' and about two weeks earlier than 'Hiratsukared' at a harvest time, in different production locations. Blooming and harvest dates were Apr. 28 and Aug. 6 in 1988, respectively, at the Nagano Fruit Tree Experimental Station. Accordingly, the tree is suitable as a cultivar.

BOTANICAL DESCRIPTION OF THE CLAIMED PLANT

Figure 1:
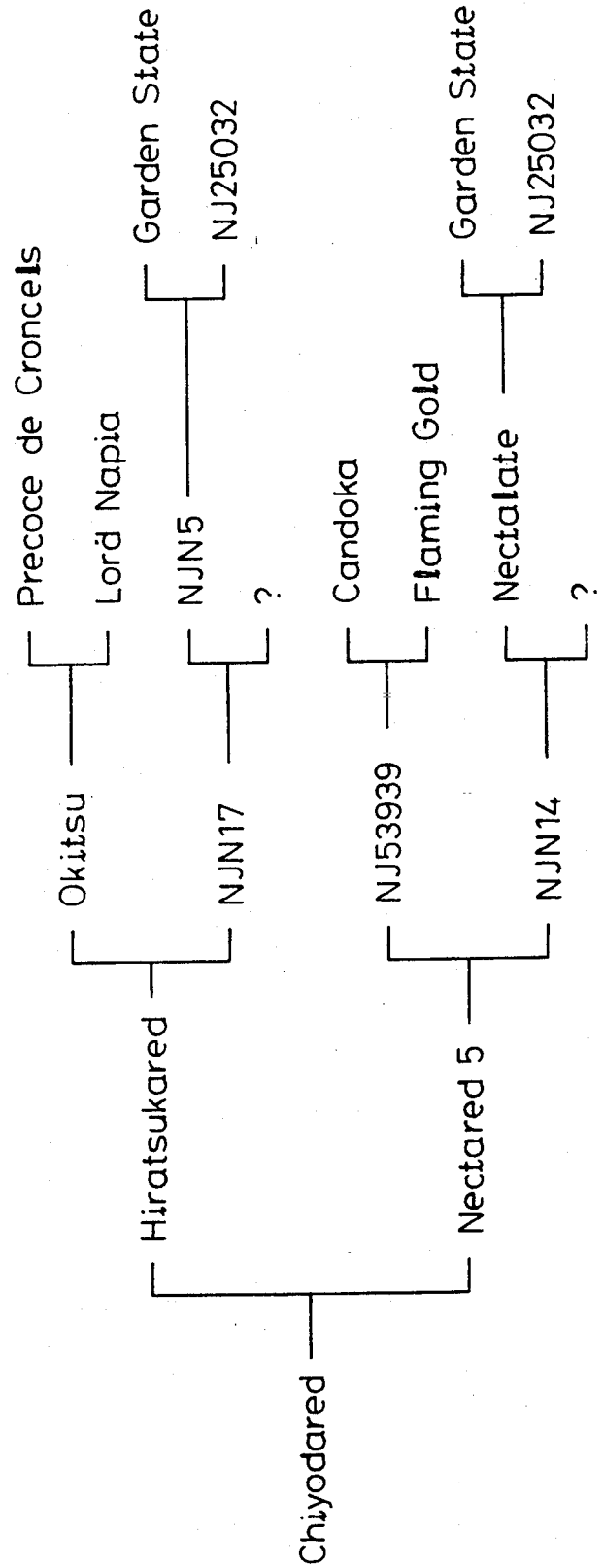
FIG. 1 shows the pedigree of the new and distinct variety of nectarine tree 'Chiyodared'.
Figure 2:
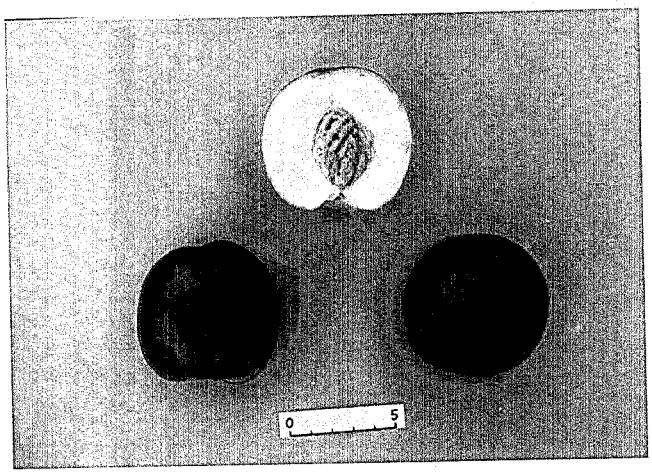
FIG. 2 is a photograph showing mature fruit of the variety taken from the blossom end, and a side view.
Figure 3:
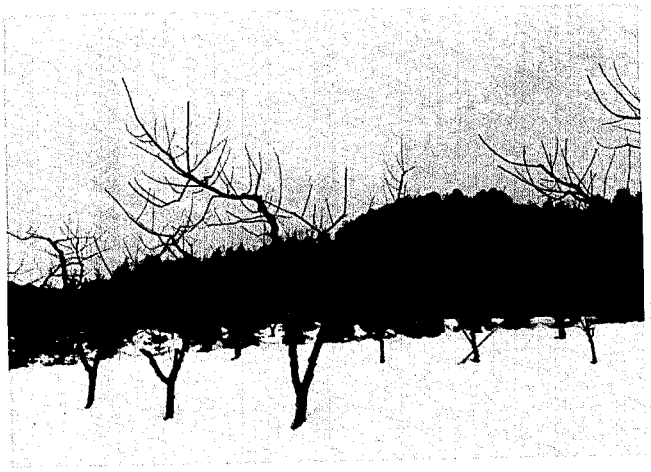
FIG. 3 is a photograph of a shape of the tree.
Figure 4A:
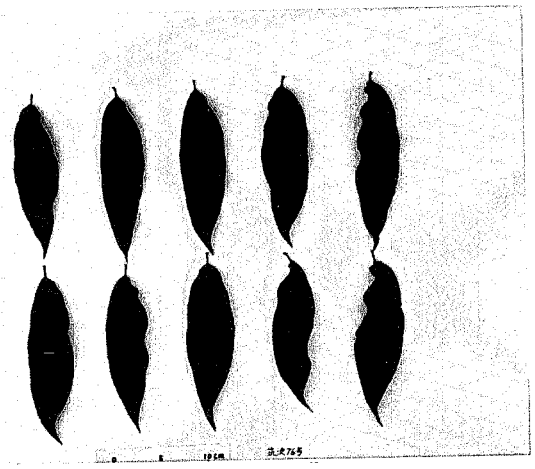
FIGS. 4(*al ) and (b*) are photographs of adult leaves, (a) adaxial and (b) abaxial, respectively.
Figure 4B:
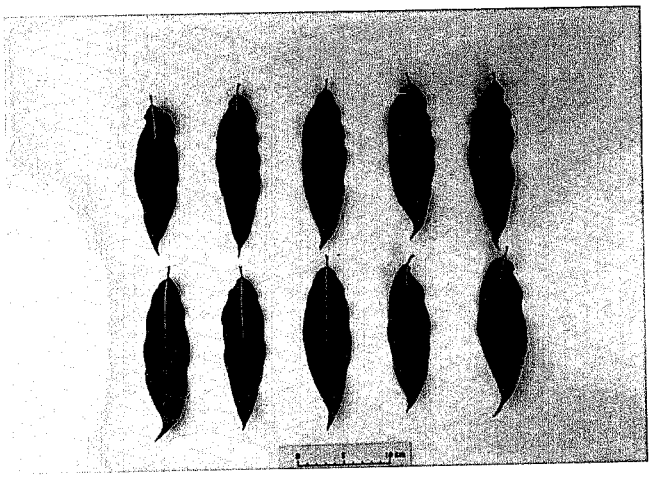
Figure 5:
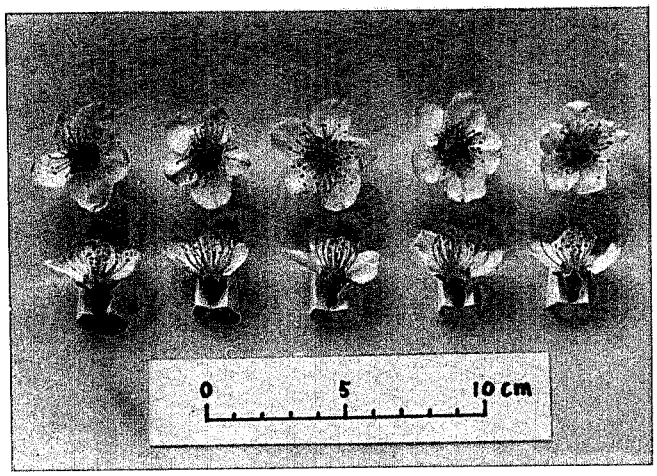
FIG. 5 is a photograph of the flower of the tree.
Figure 6A:
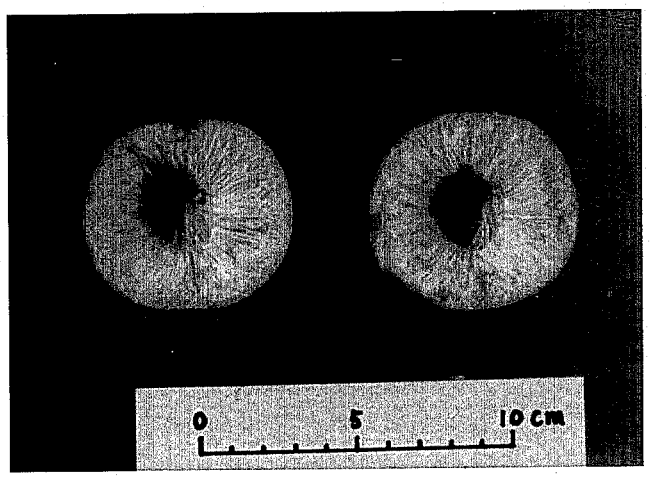
FIGS. 6(*a*) and (*b*) are photographs of cross-sectional views and longitudinal-sectional views of the fruit of the tree, respectively.
Figure 6B:
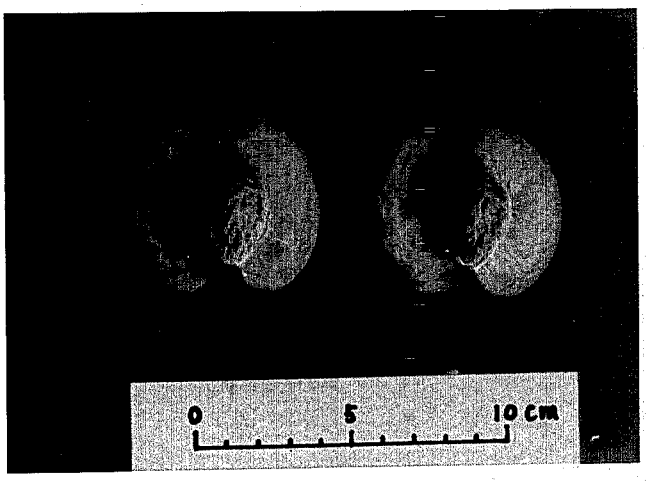

The characteristics of the new and distinct variety of nectarine (*Prunis persica*) 'Chiyodared' are as follows:

Tree:

*Habit of branches.*—Medium spreading (i.e., 5-5.5 meters in height and 6-6.5 meters in width in an appropriately pruned specimen 8-10 years old); same as 'Hiratsukared'. If an unpruned specimen 8-10 years old is observed, the tree may have a height of about 7 meters and a width of about 7 meters. The tree must be pruned. The bark texture of the new and old wood was smooth and had a high density, and was slightly smooth and had a moderate density, respectively. The characteristics of lenticels of the new wood were slightly large and oblong, and slightly rough in density. When the tree was grafted on a wild-type peach, the tree grew to about 5 meters in height and about 5 meters in width in over 5 years.

*Vigor.*—Slightly strong; stronger than 'Wase-nectarine', but weaker than 'Hiratsukared'.

*Thickness of shoot.*—Slightly shout; thicker than 'Wase-nectarine', but more slender than 'Hiratsukared'.

*Length of internode.*—Medium (26.5 mm); same as 'Wase-necatrine'.

*Ground color of shoot.*—Green (J.H.S.C. 3513; ISCC-NBS, moderate yellow green); changed to reddish brown (J.H.S.C. 0410; ISCC-NBS, dark red) by sun.

*Predominance of flower bud.*—Medium; mixed single and multiple buds, in contrast to 'Wase-nectarine' and 'Hiratsukared' with multiple buds.

*Productivity.*—Moderate productivity, i.e., about 60 kg of fruit harvested per tree, based upon an adult tree, and alternate bearing is not observed.

*Fertility.*—The tree is self-fertile, and does not require a pollinating variety.

Leaves:

*Shape.*—Elongated; same as 'Wase-nectarine' and 'Hiratsukared'.

*Size.*—Large (173 mm×47 mm); same as 'Wase-nectarine'; but smaller than 'Hiratsukared'.

*Color.*—Top and under side is yellowish green (J.H.S.C. 3309; USCC-NBS, dark olive green); same as 'Wase-nectarine' and 'Hiratsukared'.

*Serrations.*—Crenate; same as 'Wase-nectarine' and 'Hiratsukared'.

*Petiole.*—Medium; compared with other variety, green (J.H.S.C. 3307; ISCC-NBS, strong yellow green).

Flowers:

*Shape of flowerbuds.*—Reniform.

*Size.*—Uniform, large; larger than 'Wase-nectarine' and same as 'Hiratsukared', (petal: 16 mm ×17 mm).

*Number of petals.*—Single (5 petals).

*Shape of petal.*—Ovoid; same as 'Hiratsukared'.

*Color of petals.*—Pink (J.H.S.C. 0101; ISCC-NBS, pinkish white)

*Number of pistils.*—One.

*Blooming period.*—Medium; Apr. 11-Apr. 14, 1988, at above-mentioned Chiyoda-mura.

Fruit:

*Size.*—Medium; average diameter axially-about 68 mm, average transversely in suture plane—about 67 mm, average weight-about 170 g, larger than 'Wase-nectarine' but smaller than 'Hiratsukared'.

*Shape.*—Uniform, Round to round-elliptic.

*Depth of stylar end.*—Shallow; shallower than other variety.

*Depth of stalk cavity.*—Slightly shallow; average 4 mm, between 'Wase-nectarine' and 'Hiratsukared'.

*Breadth of stalk cavity.*—Slightly narrow; average diameter 10 mm.

*Suture at stylar end.*—Shallow.

*Maturity.*—Ripening early in season; best time for picking on Jul. 15, 1988, at Tsukuba as stated above. The ripening of tissues, within the fruit is even, but at the stalk end, 2 or 3 days late. The ripening of the fruit on individual trees in even.

*Storage and shipping qualities.*—The storage and shipping qualities of the fruit are as good as those of 'Nectared 5'.

Skin:

*Thickness.*—0.5 mm.

*Ground color.*—Yellow (J.H.S.C. 2506)

*Type of overall color of skin.*—Deep red (J.H.S.C. 0408)

*Form of overall color of skin.*—Solid.

*Intensity of overall color of skin.*—Deep; deeper than 1 Hiratsukared'.

*Tendency to crack.*—Little; less than 'Wase-nectarine'.

Flesh:

*Texture.*—Medium, Melting; softer than 'Wase-nectarine', same as 'Hiratsukared'. The amount of the fruit fibers is slightly abundant, and the tenderness of same is slightly hard.

*Browning of the flesh.*—Slight.

*Juiciness.*—Juicy; juice having pH of about 3.5. The juiciness equals that of 'Wase-Nectarine' and 'Hiratsukared'.

*Color.*—Yellow (J.H.S.C. 2204; ISCC-NBS, brilliant yellow); slightly red (J.H.S.C. 0707; ISCC-NBS, vivid red) near pit. The fruit has a few red striations in the flesh and a small pit cavity.

*Acidity of the flesh.*—Strong; slightly stronger than 'Wase-nectarine'.

*Flavor.*—The taste and eating quality of the flesh is moderately sweet and heavily sub-acid, tart. Fruit is of characteristic, but mild nectarine flavor, and attaining a high degree of sweetness with little astringency when allowed to attain full ripeness on the tree.

*Astringency.*—None.

Stone:

*Type.*—Clingstone.

*Size.*—Medium; average length-about 40 mm, average breadth-about 26 mm.

*Shape.*—Obovoid.

*Tendency to split.*—Slight.

*Color.*—Light brown (J.H.S.C. 1908; ISC-NBS, deep orange yellow).

Use:

*Market.*—Dessert.

Resistance to insects and diseases: No unusual susceptibilities noted.

Cold resistance: Medium.

The nectarine tree and the fruit thereof herein described may vary slightly due to the climatic and soil conditions under which the variety is grown. This description is of a variety as grown at the Fruit Tree Research Station, Ministry of Agriculture, Forestry and Fisheries, at 2-1, Fujimoto, Tsukuba-shi, Ibaraki-ken. Japan, without other statements.

Although the fruit has a high sourness as stated above, it has a rich taste when the Brix is high and no astringency, and thus has an excellent dessert quality.

We claim:

1. A new and distinct variety of genetically nectarine (*Prunus persia*) tree, substantially as illustrated and described, which is of an early ripening cultivar, moderately vigorous, moderately spreading, foliated with large elongated yellowish-green leaves, and producing uniform, medium size, round to round-elliptic shaped, clingstone fruit having a yellow ground color and deep red over color skin, and yellow flesh which is slightly red near the pit; the variety being particularly characterized in comparison with 'Hiratsukared' (the seed parent), by fruit which ripens two weeks earlier, is slightly smaller, more sourer, and has a unique eating quality.

* * * * *